(12) United States Patent
Withey

(10) Patent No.: US 7,743,665 B2
(45) Date of Patent: Jun. 29, 2010

(54) TEST PIECE AND APPARATUS FOR TESTING

(75) Inventor: Paul Anthony Withey, Derby (GB)

(73) Assignee: Rolls-Royce PLC, London (GB)

( * ) Notice: Subject to any disclaimer, the term of this patent is extended or adjusted under 35 U.S.C. 154(b) by 137 days.

(21) Appl. No.: 12/153,521

(22) Filed: May 20, 2008

(65) Prior Publication Data

US 2008/0307910 A1    Dec. 18, 2008

(30) Foreign Application Priority Data

Jun. 15, 2007   (GB) .................... 0711583.5

(51) Int. Cl.
*G01B 5/30* (2006.01)
(52) U.S. Cl. .................... 73/760; 73/856
(58) Field of Classification Search ............ 73/760, 73/856
See application file for complete search history.

(56) References Cited

U.S. PATENT DOCUMENTS

| | | | | |
|---|---|---|---|---|
| 4,408,884 A | * | 10/1983 | Kleinknecht et al. | ........ 356/496 |
| 4,796,465 A | * | 1/1989 | Carreno et al. | ........... 73/112.01 |
| 4,836,031 A | * | 6/1989 | Jatho et al. | ..................... 73/800 |
| 5,054,324 A | * | 10/1991 | Pohl | ............................ 73/859 |
| 5,056,370 A | * | 10/1991 | Maier | ........................... 73/794 |
| 5,176,028 A | * | 1/1993 | Humphrey | ................ 73/150 A |
| 5,176,061 A | * | 1/1993 | Mano | ........................... 83/684 |
| 5,994,144 A | * | 11/1999 | Nakajima et al. | ........... 436/116 |
| 2008/0028825 A1 | * | 2/2008 | Powers et al. | .............. 73/12.09 |

FOREIGN PATENT DOCUMENTS

| | | |
|---|---|---|
| FR | 2 638 525 | 5/1990 |
| JP | A-2-108942 | 4/1990 |
| JP | A-9-318514 | 12/1997 |

* cited by examiner

*Primary Examiner*—Max Noori
(74) *Attorney, Agent, or Firm*—Oliff & Berridge, PLC

(57) ABSTRACT

A test piece for mechanical property testing, the test piece is generally elongate having two opposing surfaces. Each surface comprises at least one integral loading land. Preferably there are two lands on one surface and one or two on the other for three- or four-point bending testing.

10 Claims, 1 Drawing Sheet

TEST PIECE AND APPARATUS FOR TESTING

The present invention relates to test pieces and apparatus for performing mechanical property testing of such test pieces. It particularly relates to ceramic test pieces at elevated temperatures but may be applied to room temperature tests.

Ceramic materials are used for many devices that are subjected to loads and stresses during operation. Prior to introduction of such a device it is important to test the material to ensure it can withstand the anticipated loads within a suitable safety margin. Mechanical property testing is conducted to determine the behaviour of a representative sample of the material, usually a rectangular cross-section elongate bar. Typically the testing comprises a modulus of rupture test, commonly known as a three- or four-point bending test, and a creep test. The apparatus for these tests may be substantially the same. In a modulus of rupture test loading is applied to determine the breaking force of the test piece. In a creep test the test piece is loaded at less than its breaking force for a prescribed length of time and the deflection of the test piece measured.

One conventional test piece geometry and corresponding apparatus is described in JP 2,108,942 and closely mirrors the requirements of BS1902. The test piece is a rectangular cross-section elongate ceramic bar. The testing apparatus comprises a chamber having a load bed, on which the test piece is placed, having two cylindrical rollers for location on each end of the test piece. Typically the cylindrical rollers are longer than the width of the test piece so as to extend beyond its longitudinal edges. Alternatively hemi-cylindrical protrusions integrally formed with or attached to the load bed may be substituted for the rollers. A third roller, in the case of a three-point bending test as shown in JP 2,108,942, is disposed above the test piece approximately half way along its length and equidistant from each of the other rollers. Loading means are provided above the third roller to apply the loading to the test piece.

JP 9,318,514 discloses a similar arrangement in which the test piece is located within a furnace and is heated before loading occurs. Typically the furnace is heated and then a test piece is inserted into the furnace through a small, sealable aperture resembling a letterbox. It is then allowed to soak in the heat for a prescribed period and is finally loaded.

One disadvantage of this arrangement is that it is difficult to align the test piece correctly when inserting it through the small aperture. The tests and relative sizes of the test piece and rollers are designed on the assumption that the test piece and rollers are at right angles to each other. If the test piece is misaligned the contact area with the rollers is increased and, in extreme cases, the end of a roller may be located against the test piece instead of beyond its edge. In either of these situations the flexural behaviour of the test piece is adversely affected and an incorrect breaking force recorded.

This problem is further compounded in a heated furnace in which testing may take place at around 1600° C. or even higher for some material applications. Typically a window may be provided into the chamber but it is difficult to provide a window that can safely withstand such temperatures. Furthermore, if such a window is provided the radiation substantially obscure the view of the test piece and so visual correction of the alignment is generally impractical.

Thus the present invention seeks to provide a novel geometry for a test piece and the corresponding test piece apparatus that seeks to address the aforementioned problems.

Accordingly the present invention provides a ceramic test piece for mechanical property testing, the test piece is generally elongate and defines two opposing surfaces characterised in that each surface comprises at least one integral loading land.

Preferably the test piece is generally rectangular in cross-section.

Preferably the ceramic test piece is cast.

Preferably each of the at least one integral loading lands is elongate and extends between opposite lateral edges of the test piece. Preferably each of the at least one integral loading lands is generally semi-ellipsoidal in cross-section. Alternatively each of the at least one integral loading lands is generally rectangular or triangular in cross-section.

Preferably the test piece comprises one integral loading land on one of the opposed surfaces and two integral loading lands on the other of the opposed surface. Alternatively the test piece comprises two integral loading lands on each of the opposed surfaces.

The present invention will be more fully described by way of example with reference to the accompanying drawings, in which.

Figure 1:
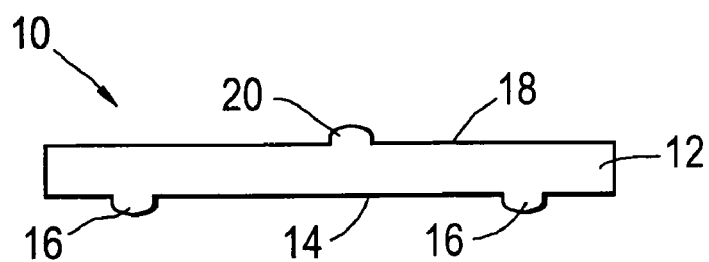
FIG. 1 is a schematic side view of an exemplary embodiment of a test piece according to the present invention.

An exemplary embodiment of a test piece according to the present invention is shown in FIG. 1. A test piece 10 is shown in cross-section. It comprises a rectangular bar 12 that is typically 100 mm long, 12 mm wide (into the page) and 4 mm thick. Located on a first surface 14, the lower surface of the bar 12, is a pair of loading lands 16 spaced apart from one another. Each loading land 16 is located towards one end of the test piece 10. The loading lands are in the form of hemi-cylindrical lands that extend across the width of the test piece 10. In use, the loading lands 16 provide the loading location instead of the rollers of the prior art arrangement. Located on the second surface 18, the upper surface of the bar 12, is another loading land 20 that is positioned approximately half way along the bar 12. This loading land 20 is also a hemi-cylindrical land that extends across the width of the test piece 10. In use, loading land 20 is provided instead of the upper roller of the prior art arrangement.

Thus there are provided three integrally formed loading lands 16, 20. Typically the diameter of each is between 1 mm and 5 mm. Preferably all the loading lands 16, 20 are the same diameter, for example 5 mm. Alternatively the upper loading land 20 may be a different diameter, for example 2 mm. These diameters are substantially the same as the rollers of the prior art arrangement.

The test piece is manufactured from ceramic. A simple modification to the mould of a prior test piece is sufficient to provide the geometry of the present invention. Due to the small size of the loading lands 14, 20, little extra material is required compared to prior test pieces and so it is simple and relatively cheap to manufacture test pieces having the shape of the present invention.

Figure 2:
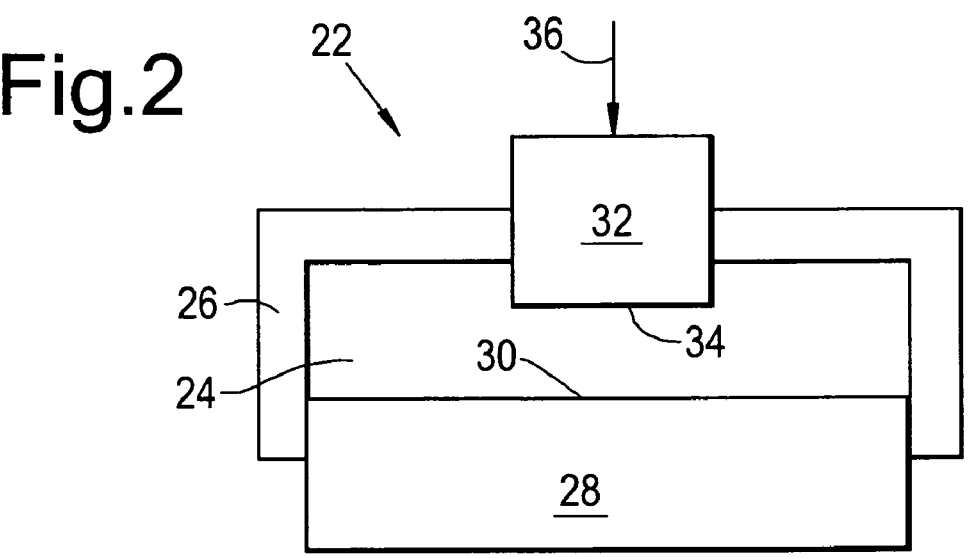
FIG. 2 is a schematic side view of apparatus according to the present invention.

FIG. 2 shows mechanical property testing apparatus 22 suitable for testing a test piece 10 according to aspects of the present invention. The apparatus comprises a testing chamber 24 that is defined by walls 26, loading bed 28 and loading means 32. The present invention finds particular utility in mechanical property testing of ceramics at high temperatures.

Therefore, the chamber 24 is heated by any suitable heating means (not shown) located either internally or externally of the chamber 24.

The loading bed 28 is a relatively massive block with a substantially flat upper surface 30 that forms the base of the chamber 24. In use, a test piece 10 is positioned on the upper surface 30 of the loading bed 28 so that the lower loading lands 16 abut the upper surface 30 of the loading bed 28. Since the loading lands 16 are hemi-cylindrical the abutment, and therefore the loading, is along a line with substantially no lateral width. Thus, the loading behaviour is the same as the prior art arrangement having rollers but is easier to control. The loading bed 28 is larger, in length and width, than the test piece 10 so that the test piece 10 does not abut any of the walls 26 when located in the chamber 24.

The loading means 32 comprises a solid block having a substantially flat lower surface 34 positioned substantially parallel to and spaced apart from the upper surface 30 of the loading bed 28. The loading means 32 are moveable by any suitable means (not shown) towards the loading bed 28 to abut the upper loading land 20 of the test piece 10. The loading means 32 is then moved further towards the loading bed 28 to exert a loading force, indicated by arrow 36, onto the upper loading land 20 of the test piece 10. As with the lower loading lands 16, the loading behaviour is substantially the same as with the prior art rollers. The loading means 32 is a block that is wider than the upper loading land 20 and is long enough to extend substantially to either side of the upper loading land 20.

A small sealable aperture (not shown) is provided in one of the walls 26 of the chamber 24 to enable the test piece 10 to be inserted into the chamber 24. However, unlike the prior art arrangement, there is no requirement to precisely align the test piece 10 with rollers to ensure the loading is applied as designed. Since the loading bed 28 and loading means 32 are larger than the test piece 10, and their opposed surfaces 30, 34 are flat, it is possible to achieve the correct loading behaviour even when the test piece 10 is not positioned at right angles to the apparatus 22. This is an advantage over the prior art arrangements as it enables test pieces 10 to be inserted with less accuracy and greater speed whilst improving the quality of the results produced and offering greater confidence that the three-point bending test has occurred correctly.

Figure 3:
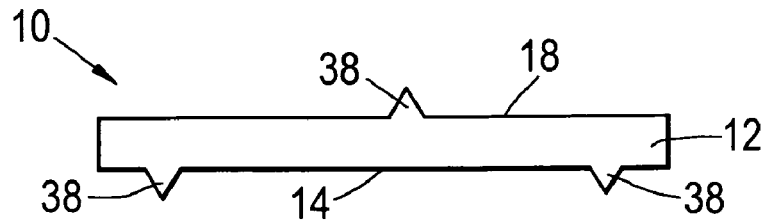
FIG. 3 is a schematic side view of a second embodiment of a test piece according to the present invention.
Figure 4:
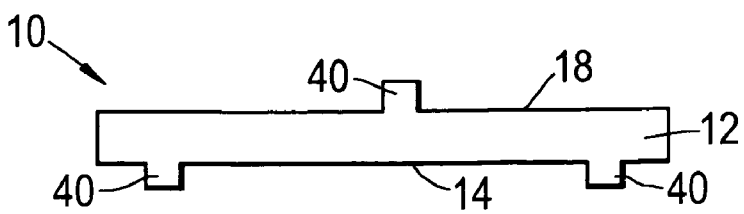
FIG. 4 is a schematic side view of a third embodiment of a test piece according to the present invention.

FIG. 3 and FIG. 4 show alternative embodiments of the test piece 10 of the present invention. Each test piece comprises an elongate, rectangular bar 12 with integral loading lands located as described with respect to FIG. 1. In FIG. 3, the loading lands 38 are triangular in cross-section and thus are triangular prisms extending across the width of the test piece 10. This arrangement ensures that the loading is a true knife-edge, or two-dimensional line, loading.

In FIG. 4, the loading lands 40 are square or rectangular in cross-section and thus are cuboids extending across the width of the test piece 10. These loading lands 40 may be preferable to triangular or cylindrical lands as there is a greater contact surface and therefore less compressive load passes through them. Thus, with certain ceramics of less compressive resistance, this configuration may be preferable.

It will be clear to the skilled reader that further modifications may be made without departing from the scope of the invention claimed. For example, alternative shapes for the loading lands may be contemplated. The loading lands may extend across only part of the width of the test piece. Preferably in this instance the loading lands would extend across most of the width and be symmetrical about the centre line of the test piece.

Although the present invention has been described with respect to a heated test environment, the benefits of the test piece and apparatus construction may equally be derived in room temperature or chilled testing.

Although three-point loading has been described it is possible to modify the test piece of the present invention to have four loading lands to enable four-point loading.

Although the load bed 28 has been described as a relatively massive single block it could also be two pieces spaced apart, or have a hole or channel through the middle. This enables the test piece 10 to drop out of the hot chamber 24 of the testing apparatus 22 once testing is completed and the test piece 10 broken.

The invention claimed is:

1. A ceramic test piece for mechanical property testing, the test piece is generally elongate and defines two opposing surfaces, characterised in that each surface comprises at least one integral loading land wherein the loading lands are protrusions from each surface.

2. A ceramic test piece as claimed in claim 1 wherein the test piece is generally rectangular in cross-section.

3. A ceramic test piece as claimed in claim 1 wherein the test piece is cast.

4. A ceramic test piece as claimed in claim 1 wherein each of the at least one integral loading lands is elongate and extends between opposite lateral edges of the test piece.

5. A ceramic test piece as claimed in claim 1 wherein each of the at least one integral loading lands is generally hemi-spherical in cross-section.

6. A ceramic test piece as claimed in claim 1 wherein each of the at least one integral loading lands is generally semi-ellipsoidal in cross-section.

7. A ceramic test piece as claimed in claim 1 wherein each of the at least one integral loading lands is generally rectangular in cross-section.

8. A ceramic test piece as claimed in claim 1 wherein each of the at least one integral loading lands is generally triangular in cross-section.

9. A ceramic test piece as claimed in claim 1 wherein the test piece comprises one integral loading land on one of the opposed surfaces and two integral loading lands on the other of the opposed surfaces.

10. A ceramic test piece as claimed in claim 1 wherein the test piece comprises two integral loading lands on each of the opposed surfaces.

* * * * *